United States Patent [19]
Hull

[11] Patent Number: 5,259,984
[45] Date of Patent: Nov. 9, 1993

[54] RINSE-FREE CLEANSING COMPOSITION

[75] Inventor: James W. Hull, Mt. Carmel, Ill.

[73] Assignee: Jim Hull Associates, Inc., Mt. Carmel, Ill.

[21] Appl. No.: 881,205

[22] Filed: May 11, 1992

[51] Int. Cl.$^5$ .............. C11D 3/37; C11D 3/60; B08B 5/04; B08B 7/00
[52] U.S. Cl. .................. 252/174.17; 134/4; 134/21; 134/40; 252/158; 252/174.21; 252/544; 252/546; 252/DIG. 2; 252/DIG. 5; 252/DIG. 19
[58] Field of Search ............ 252/DIG. 5, DIG. 19, 252/174.17, 174.21, 544, 546, 158, DIG. 2; 134/40, 21, 4

[56] References Cited

U.S. PATENT DOCUMENTS

| | | | |
|---|---|---|---|
| 2,227,321 | 12/1940 | Robson | 252/DIG. 5 |
| 2,410,168 | 10/1946 | Kleinicke | 252/173 |
| 2,525,303 | 10/1950 | Lenoble | 252/DIG. 5 |
| 2,546,383 | 3/1951 | Blumberg | 252/165 |
| 2,567,999 | 9/1951 | Guastavino | 252/118 |
| 3,277,013 | 10/1966 | Gianladis | 252/153 |
| 3,634,265 | 1/1972 | Merritt | 252/153 |
| 4,594,362 | 6/1986 | Smith et al. | 521/52 |
| 4,659,494 | 4/1987 | Soldanski et al. | 252/88 |
| 4,673,526 | 6/1987 | Zabotto et al. | 252/174.16 |
| 4,678,606 | 7/1987 | Akhter et al. | 252/542 |
| 4,690,779 | 9/1987 | Baker et al. | 252/546 |
| 4,693,755 | 9/1987 | Erzinger | 134/4 |
| 4,765,922 | 8/1988 | Contamin et al. | 252/90 |
| 4,834,900 | 5/1989 | Soldanski et al. | 252/88 |
| 4,917,823 | 4/1990 | Maile, Jr. | 252/548 |

FOREIGN PATENT DOCUMENTS

| | | |
|---|---|---|
| 9105837 | 5/1991 | PCT Int'l Appl. |
| 0842866 | 7/1960 | United Kingdom |
| 1540386 | 2/1979 | United Kingdom |
| 2179052 | 2/1987 | United Kingdom |

OTHER PUBLICATIONS

Jellinek, Dr. Stephan *Formulation and Function of Cosmetics*, New York, John Wiley & Sons, 1970, pp. 223–226, 234–236.
"Waterless Hand Cleaners", M. Lesser in Soap and Sanitary Chemicals, Apr. 1948, pp. 48–50 & 181.
"Waterless Hand Cleaners," M. Lesser in Drug and Cosmetic Industry, Mar. 1953, pp. 326, 327 & 408–414.
Derwent abstract accession No. 91-148718/20, WO 9105837 (May 1991).
Lavotex Publication, "Soaping Up", Consumer Reports, Oct. 1990, pp. 644–647.

*Primary Examiner*—Paul Lieberman
*Assistant Examiner*—Ardith Hertzog
*Attorney, Agent, or Firm*—Lockwood, Alex, FitzGibbon & Cummings

[57] ABSTRACT

A rinse-free cleaner composition is provided in a composition comprising a storage-stable volatile polymer gel solution and a cleaning agent including an alkali metal hydroxide. In a preferred embodiment, the polymer gel solution includes a hydroxypropylmethylcellulose polymer and has a lotion-like consistency when stored in a closed container until ready for use. After being applied to a surface and being exposed to air and rubbing, the cleaner composition beads up, extracting dirt, oil, grease and foreign particles, and falls off without the need for a towel and easily wipes away to provide a substantially cleaned, micro-film coated surface.

19 Claims, No Drawings

RINSE-FREE CLEANSING COMPOSITION

BACKGROUND OF THE INVENTION

The present invention generally relates to cleaners which may be employed to clean a variety of surfaces, without the need to use water for rinsing. More particularly, it relates to a new and improved spreadable gel cleaner composition for cleaning surfaces such as hands, upholstery or carpet which may be rubbed in a thin layer onto the surface to be cleaned and upon exposure to the air and continued rubbing, beads up into small soft particles capable of being brushed or wiped away thereby carrying dirt, oils and foreign matter with the gel particles away from the surface, much like "art-gum".

A variety of cleaning compositions commonly employ soaps or detergents in water to remove dirt or grease. For example, upholstery has been cleaned by foamable water-based surfactant systems. However, this method has the disadvantage that the wetting of the surface may drive the dirt further into the upholstery. Moreover, the cleansing agent must be given time to dry before it can be removed. In addition, water-based soaps for use on hands generally require the availability of a sink and water for rinsing off the soap and a towel, rag or cloth to dry.

Oil based cleaners which rely on emulsion action systems and emulsifying detergents are generally not completely successful in removing dirt from surfaces and most require water rinsing and towel drying for satisfactory removal.

Hand cleaners which may be used without the need for water for rinsing are known. In U.S. Pat. No. 2,548,383, for example, soya bean oil is combined with a petroleum solvent in order to convert the fatty oil to a solid colloidal form. A process for making an oil based composition is both timely and difficult. Accordingly, a need still exists for additional cleaners which can remove soils, grease and stains from a wide variety of surfaces without the need of water for rinsing and/or a towel for wiping or drying. The cleaner preferably is not oil based and will not leave an undesirable residue, but rather will leave a desirable micro-film layer of gel polymer which may or may not further include emollients or other additives.

In order to overcome the deficiencies of the prior art compositions, it is an object of the present invention to provide a new and improved cleaner composition which will bead up upon exposure to air and upon rubbing so that a water rinse or towel is unneeded.

It is another object of the present invention to provide a new and improved cleaner composition which may be used on many surfaces including hands, upholstery, carpet, and the like.

It is a further object of the invention to provide a new and improved rinse-free cleaner composition which may be used to remove many substances such as tar, ink, ballpoint pen ink, grease, pencil, carbon paper, fresh paint, fish odor, and animal husbandry odor simply by rubbing the cleaner on and continuing the rubbing until the cleaner together with the bound substance to be removed beads up and falls off like art-gum.

It is another object of the invention to provide a new and improved cleaner composition which may be used in many places where water is not readily available or where its use would be undesirable.

It is still a further object of the present invention to provide a new and improved composition comprising a film-like, germ-proof barrier which may be used as a temporary glove.

SUMMARY OF THE INVENTION

In accordance with these and other objects, the present invention provides a new and improved spread-on/rub-off, rinse-free cleaner composition. The cleaner composition comprises a storage stable hydroxyalkyl-methylcellulose polymer gel solution having a spreadable lotion-like consistency, a cleaning agent including an alkali metal hydroxide and a volatilizing agent which increases the rate of evaporation of the composition upon exposure to air at room temperature. The cleaner composition is spreadable onto a surface to be cleaned. The cleaner composition absorbs and extracts dirt, oils and foreign particles disposed on the surface. Upon exposure to air and continuous rubbing, the viscosity of the cleaner composition increases rapidly such that the composition beads up and rolls off of the surface without the need for water rinsing or further drying, to provide a cleaned surface.

In accordance with this inventive composition, the polymer gel is dispersed in the cleaning agent and volatilizing agent to form a cleaner composition having a spreadable lotion-like consistency which is stable on storage in a closed container. The composition includes a volatilizing agent which aids in increasing the evaporation rate of the aqueous solvent mixture when exposed to air. Upon exposure to air and rubbing, the cleaner composition loses water and the co-evaporating volatilizing agent. As the evaporation proceeds, the viscosity of the polymer gel composition increases. The increased viscosity causes the polymer gel to become tacky and self-adherent causing dirt and oils to be lifted from the surface to be cleaned and bound up into the tacky polymer phase. Upon further evaporation and rubbing, the polymer gel particles become harder and drier so that they become less sticky. Eventually, the cleaner composition beads up and rolls off the surface without the need for water rinsing or drying, leaving substantially no residue, but a smooth satin feel.

In accordance with this invention, the cleaning agent portion of the cleaner composition preferably comprises an alkali metal hydroxide, a non-ionic surfactant, a polymeric polyol, a chelating agent and a liquid polyamine. In a preferred embodiment the cleaning agent portion is provided in the form of a premixed solution.

In accordance with the preferred embodiment, the volatilizing agent comprises a $C_1$-$C_6$ straight or branched chain alcohol in an amount sufficient to increase the evaporation rate of the aqueous polymer gel composition to provide a desired increase in the viscosity of the overall cleaner composition such that it beads-up into soft solid particles and thereafter rubs off in less than approximately five minutes. The evaporation rate may be varied by increasing or decreasing the amount of volatilizing agent present.

The new and improved cleaner composition of the present invention may advantageously be used on both hands and other surfaces such as upholstery and carpeting. For hand cleaning uses, the cleaner is ideal for field situations where running water and drying towel are not available. Generally, the cleaner is applied from a tube, jar or pump bottle onto the hands or other surface and rubbed to remove dirt and cause the cleaner to bead up. Thereafter, the dirt and cleaner may simply be wiped or vacuumed away. When employed as a spot cleaner for upholstery or carpeting, the cleaner composition is applied from the container tube onto a dirty spot and rubbed with a brush or by hand to permit the cleaner to dissolve or lift the spot from the fabric into the polymer matrix without unnecessarily wetting the carpet or upholstery area. Continued rubbing or brushing of the cleaner into the spot causes the spot and the cleaner to bead up so that it can be wiped, swept or vacuumed away from the surface.

In accordance with an especially preferred embodiment of the invention, a plasticizer may be added to the composition to provide a film-like substance capable of forming a germ-proof, water-proof barrier. This barrier may be formed over a hand to provide a flexible, filmed glove to provide a sterile barrier for the hand. This barrier may temporarily protect the hands from dirt and germs while performing given working tasks and later all may be washed away with water or may be rubbed off to remove the dirt and germs. Glycerine is a preferred plasticizer for this alternate embodiment, but other plasticizers such as polyethylene glycol may also work. Other compounds and ingredients may be added to the composition such as abrasive fillers, salts to lower the effective gel point of the solution and other viscosity modifying agents. The cleaning composition in accordance with this invention leaves a satin-like microcoating on the skin and accordingly, it may be desirable to add medicines, antiseptic agents or bactericides to prevent the spread of germs.

Other objects and advantages provided by the present invention will become apparent from the following Detailed Description of the Invention and Examples.

DETAILED DESCRIPTION OF THE INVENTION

More particularly, the cleaner composition of the present invention comprises a volatile aqueous polymer gel component. Illustrative aqueous polymer gels may include: cellulose gels, polymer latexes, and other hydrophilic polymeric thickening agents. Film-forming agents such as neoprene latex, styrene copolymer latex, polyvinyl alcohol (PVA) and polyvinyl-chloride (PVC) latex, may be employed to prepare an aqueous polymer gel component for use herein. A preferred gel component comprises an aqueous hydroxyalkylmethylcellulose-based polymeric gel. Hydroxypropylmethylcellulose is especially preferred. The preferred cellulose ether gelling agent is effective to thicken an aqueous solution to provide a smooth lotion-like, spreadable gel consistency when added in a minor effective amount of from about 1% to about 20% by weight of the overall composition. Preferably, the gelling agent polymer will have a viscosity of at least about 3,000–6,000 centipoises when measured as a 2% solution at 25° C. Moreover, the gelling agent has an average particle size of at least about 50 microns.

In accordance with the preferred embodiment, the gelling agent employed is Methocel ® E50-LV, available from Dow Chemical Company. Methocel ® E50-LV is a hydroxypropylmethylcellulose polymer composition comprising about 97% by weight methyl cellulose polymer, 2% weight water and 1% by weight sodium chloride. Methocel ® has an average particle size of $\geq 50$ microns and has a standard viscosity of about 4,000 cP. (2% solution at 25° C.). In accordance with the preferred embodiment, Methocel ® gelling agent is added in an effective gelling amount of from about 2.0 to about 10% by weight, based on the weight of the overall cleaner composition. Hydroxypropylmethylcellulose gelling agents are preferred because of their advantageous freeze-thaw properties.

In accordance with the present invention, the cleaner composition also comprises a minor effective amount of a volatilizing agent. The volatilizing agent should be an additive which when added to the aqueous polymer gel composition increases the evaporation rate of the aqueous solvent portions as compared to the same composition not containing the volatilizing agent. Preferred volatilizing agents for use herein are monohydric or polyhydric alcohols. Preferably, the volatilizing agent is a $C_1$–$C_6$ lower hydrocarbon straight or branched alcohol. Especially preferred volatilizing agents are isopropyl alcohol and methanol, alone or in combination, which not only help to increase the rate of evaporation and related increase in cleaner viscosity, but also aid in solubilizing the hydroxypropylmethylcellulose gel forming agent in water. Preferably the volatilizing agent is added in an amount of from about 1% to about 40% by weight of the overall composition. In accordance with the preferred embodiment herein, the volatilizing agent comprises a mixture of about 4% by weight methanol and 10% by weight isopropanol based on the weight of the overall composition.

In accordance with the present invention the cleaning composition includes not only the volatile aqueous polymer gel component, but also a mixed cleaner component. The cleaner component is added preferably in the form of a pre-mixed solution. The pre-mixed solution includes an alkali metal hydroxide and optionally but preferably a non-ionic surfactant, a polymeric polyol, a chelating agent and a liquid polyamine.

Prepared in its separate components, the cleaner component includes an alkali metal hydroxide such as lithium hydroxide, sodium hydroxide or potassium hydroxide added in an amount sufficient to provide an overall pH to the composition of between 9.0 to 12.0. In the preferred embodiment the cleaner composition of the invention comprises 0.44% by weight sodium hydroxide (Occidental Chemical Corporation).

The cleaner component in accordance with the preferred embodiment includes a non-ionic surfactant such as an ethylene oxide ester of a $C_9$–$C_{10}$ alkylphenol available commercially under the tradename Triton N-101 ® (Rohm and Haas). In the preferred embodiment, the cleaner composition of the invention comprises about 2.4% by weight non-ionic surfactant.

The cleaner component preferably further includes a polymeric polyol such as a mono butyl ether of ethylene glycol, sold commercially as DOWANOL EB ® (Dow Chemical Company). In the preferred embodiment the cleaner composition comprises about 2% by weight polymeric polyol.

The cleaner component of the preferred embodiment also includes a chelating agent such as tetrasodium salt of ethylene diamine tetraacetic acid (EDTA), sold commercially as Versene 100 ® (Dow Chemical Company). In the preferred embodiment the cleaner composition of the invention comprises about 1.5% by weight chelating agent.

The base further includes a liquid polyamine, such as HA-20 ® (Emulsions Systems Inc.). In the preferred embodiment the composition of the invention comprises 2% liquid polyamine.

The pre-mixed cleaner component is added in an amount of about 30 to about 80% by weight of the overall composition. In the preferred embodiment the composition of the invention comprises 47% by weight of the pre-mixed cleaner component.

In accordance with the present invention an alternate embodiment is achieved by adding a flexibilizing agent or plasticizer in order to form a temporary glove. The plasticizer is added to the cleaning composition of the present invention in an amount sufficient to form a film-like barrier which is flexible and may be removed with considerable rubbing force or with water. The alternate embodiment includes optionally and preferably glycerine or polyethylene glycol, added to the composition in an effective film-forming amount of from about 0 to 5.0% by weight, based on the weight of the overall composition. In accordance with the preferred embodiment herein, the plasticizing agent comprises 1.4% by weight glycerine based on the weight of the overall composition. A glove-forming composition may also be prepared without added plasticizer but the resultant temporary glove will be stiffer and more brittle.

Other details concerning the preferred cleaner compositions and methods for making them are provided in the following working Examples.

DESCRIPTION OF THE PREFERRED EMBODIMENTS

EXAMPLE 1

A cleaner composition comprising a volatile aqueous gel solution and a cleaning agent was prepared as follows:

Preparation A—Pre-Mixed Cleaning Agent

A pre-mixed cleaning agent was prepared by thoroughly mixing the following ingredients until a stable pre-mixed cleaning agent component was obtained:

| INGREDIENT | PERCENT IN MIXTURE |
| --- | --- |
| Non-ionic surfactant[a] | 5.00 |
| Water | 88.00 |
| Liquid KOH | 1.50 |
| Liquid polyamine[b] | 2.00 |
| Chelating agent[c] | 1.50 |
| Polymeric polyol[d] | 2.00 |
| TOTAL CLEANER COMPONENT | 100% |

[a]Triton N-101 ®, Rohm and Haas Company
[b]HA-20 ® Amine, Emulsions Systems, Inc.
[c]Versene 100 ®, Dow Chemical Company
[d]Dowanol EB ®, Dow Chemical Company Preparation B—Volatile Aqueous Gel Solution A volatile aqueous gel solution was prepared by thoroughly mixing the following ingredients to form an aqueous gel component:

| INGREDIENT | PERCENT IN MIXTURE |
| --- | --- |
| Water | 66.9 |
| Methanol | 6.3 |
| Isopropyl Alcohol | 17.4 |
| Hydroxypropylmethyl-cellulose polymer gel[a] | 9.4 |
| TOTAL COMPOSITION | 100% |

[a]Methocel ® E50, Dow Chemical Company

A cleaner composition in accordance with the present invention was prepared by thoroughly admixing appropriate amounts of the pre-mixed cleaner component of Preparation A with the gel component of Preparation B to form the final cleaner composition set forth in Table 1 as follows:

TABLE 1

| RINSE FREE CLEANER COMPOSITION | | |
| --- | --- | --- |
| INGREDIENT | PERCENT IN MIXTURE | WEIGHT IN GRAMS |
| Non-ionic surfactant[a] | 2.42 | 12.1 |
| Water | 74.52 | 372.6 |
| Methanol | 3.74 | 18.7 |
| Isopropyl Alcohol | 10.40 | 52.0 |
| Hydroxypropylmethyl-cellulose polymer gel[b] | 5.66 | 28.3 |
| Liquid KOH | .44 | 2.2 |
| Liquid polyamine[c] | 1.00 | 5.0 |
| Chelating agent[d] | .71 | 3.55 |
| Polymeric polyol[e] | 1.11 | 5.55 |
| TOTAL COMPOSITION | 100% | 500.00 |

[a]Triton N-101 ®, Rohm and Haas Company
[b]Methocel ® E50, Dow Chemical Company
[c]HA-20 ® Amine, Emulsions Systems, Inc.
[d]Versene 100 ®, Dow Chemical Company
[e]Dowanol EB ®, Dow Chemical Company Water was admixed with non-ionic surfactant, a 45% aqueous potassium hydroxide solution, liquid polyamine, chelating agent and a polymeric polyol at a temperature of 82° C. stirring for 2 minutes. This solution was then admixed with a hydroxypropylmethylcellulose polymer gel, methanol and isopropyl alcohol solution. This solution was high in viscosity and was a good film-former. Also, the gel component dissolved easily, did not exhibit phasing or premature separation and was resistant and performed well in freeze-thaw testing.

EXAMPLE 2

A cleaner composition comprising a volatile aqueous gel solution and a cleaning agent was prepared using a premixed cleaner component in accordance with Preparation A. The cleaner composition prepared is set forth in Table 2, as follows:

TABLE 2

| CLEANER COMPOSITION | | |
| --- | --- | --- |
| INGREDIENT | PERCENT IN MIXTURE | WEIGHT IN GRAMS |
| Premixed cleaner component[a] | 46.95 | 100.0 |
| Methanol | 3.76 | 8.0 |
| Isopropyl Alcohol | 10.33 | 22.0 |
| Water | 32.86 | 70.0 |
| Hydroxypropylmethyl-cellulose polymer gel[b] | 6.10 | 13.0 |
| TOTAL COMPOSITION | 100% | 213.0 |

[a]Pre-Mixed Cleaner Component of Preparation A
[b]Methocel ® E50, Dow Chemical Company Water was admixed with methanol, isopropyl alcohol and hydroxypropylmethylcellulose polymer gel. This solution was then admixed with the premixed cleaner component. This composition was the preferred embodiment because it was an excellent film-former of high viscosity and had no phasing.

EXAMPLE 3

Another embodiment of the present invention includes the use of a plasticizer to form a film-like composition for use as a glove. A preferred embodiment was to use glycerine as the plasticizer.

The composition of this mixture is summarized in TABLE 3, as follows:

TABLE 3
TEMPORARY GLOVE CLEANER COMPOSITION

| INGREDIENT | PERCENT IN MIXTURE | WEIGHT IN GRAMS |
|---|---|---|
| Glycerine | 1.40 | 6.0 |
| Premixed cleaner component[a] | 46.51 | 200.0 |
| Methanol | 3.72 | 16.0 |
| Isopropyl Alcohol | 28.84 | 124.0 |
| Water | 13.95 | 60.0 |
| Hydroxypropylmethyl-cellulose polymer gel[b] | 5.58 | 24.0 |
| TOTAL COMPOSITION | 100% | 430.0 |

[a]Preparation A
[b]Methocel ® E50, Dow Chemical Company

Water was admixed with methanol, isopropyl alcohol and hydroxypropylmethyl cellulose polymer gel and stirred for 2 minutes. This solution was admixed with glycerine and stirred for 1 minute. Finally, this solution was admixed with the premixing cleaner component. This composition formed a very good soft film which was a germ-proof, soil-resistant barrier.

EXAMPLE 4

A cleaner composition comprising a volatile aqueous gel solution and a cleaning agent was prepared using only isopropyl alcohol. The composition of this mixture is summarized in Table 4, as follows:

TABLE 4
CLEANER COMPOSITION WITH ISOPROPYL ALCOHOL

| INGREDIENT | PERCENT IN MIXTURE | WEIGHT IN GRAMS |
|---|---|---|
| Premixed cleaner component[a] | 61.73 | 24.0 |
| Hydroxypropylmethyl-cellulose polymer gel[b] | 7.40 | 2.88 |
| Isopropyl Alcohol | 30.87 | 12.0 |
| TOTAL COMPOSITION | 100% | 38.88 |

[a]Preparation A
[b]Methocel ® E50, Dow Chemical Company

Isopropyl alcohol was admixed with hydroxypropyl methylcellulose polymer gel. This mixture was then admixed with the premixed cleaner component. The alcohol helped the Methocel ® go into solution and a high viscosity solution with good film forming properties was achieved.

EXAMPLE 5

In accordance with Example 4, a cleaner composition comprising a volatile aqueous gel solution and a cleaning agent was prepared using only Methanol. The composition of this mixture is summarized in Table 5, as follows:

TABLE 5
CLEANER COMPOSITION WITH METHANOL

| INGREDIENT | PERCENT IN MIXTURE | WEIGHT IN GRAMS |
|---|---|---|
| Premixed cleaner component[a] | 62.90 | 200.0 |
| Hydroxypropylmethyl cellulose polymer gel[b] | 5.66 | 18.0 |
| Water | 15.72 | 50.0 |
| Methanol | 15.72 | 50.0 |
| TOTAL COMPOSITION | 100% | 318.0 |

[a]Preparation A
[b]Methocel ® E50, Dow Chemical Company

Water at room temperature was admixed with methanol and hydroxypropylmethylcellulose polymer gel in a blender. This solution was then admixed with the premixed cleaner component. Similar to Example 4, the alcohol aided in putting Methocel ® into solution and achieved high viscosity.

EXAMPLE A

A cleaner composition comprising a non-volatile aqueous gel solution and a cleaning agent was prepared containing no alcohol according to Table A, as follows:

TABLE A
CLEANER COMPOSITION WITHOUT ALCOHOL

| INGREDIENT | PERCENT IN MIXTURE | WEIGHT IN GRAMS |
|---|---|---|
| Premixed cleaner component[a] | 62.90 | 200.0 |
| Hydroxypropylmethyl-cellulose polymer gel[b] | 5.66 | 18.0 |
| Water | 31.44 | 100.0 |
| TOTAL COMPOSITION | 100% | 318.0 |

[a]Preparation A
[b]Methocel ® E50, Dow Chemical Company

Water was admixed with hydroxypropylmethylcellulose polymer gel in a blender. The pre-mixed cleaner component was then admixed to the completed solution while stirring. This solution phased badly. The Methocel ® was insoluble and would not form a phase-free solution when alcohol was not present.

EXAMPLE B

A second cleaner composition comprising a non-volatile aqueous gel solution and a cleaning agent was prepared containing no alcohol according to Table B, as follows:

TABLE B
CLEANER COMPOSITION WITHOUT ALCOHOL

| INGREDIENT | PERCENT IN MIXTURE | WEIGHT IN GRAMS |
|---|---|---|
| Premixed cleaner component[a] | 99.75 | 36.0 |
| Hydroxypropylmethyl-cellulose polymer gel[b] | 0.25 | 0.09 |
| TOTAL COMPOSITION | 100% | 36.09 |

[a]Preparation A
[b]Methocel ® E50, Dow Chemical Company

The premixed cleaner component was admixed with hydroxypropylmethylcellulose polymer gel. The Methocel ® would not dissolve completely to form a solution and separated from the cleaner component.

EXAMPLE C

The cleaner composition comprising only a volatile aqueous gel solution was prepared to determine the rub-off characteristics of hydroxypropylmethylcellulose polymer gel. The composition of this mixture is summarized in Table C, as follows:

TABLE C
GEL COMPOSITION WITHOUT PRE-MIXED CLEANER

| INGREDIENT | PERCENT IN MIXTURE | WEIGHT IN GRAMS |
|---|---|---|
| Methanol | 3.76 | 8.0 |
| Isopropyl Alcohol | 10.33 | 22.0 |
| Water | 79.81 | 170.0 |
| Hydroxypropylmethyl-cellulose polymer gel[a] | 6.1 | 13.0 |

TABLE C-continued

| GEL COMPOSITION WITHOUT PRE-MIXED CLEANER | | |
|---|---|---|
| INGREDIENT | PERCENT IN MIXTURE | WEIGHT IN GRAMS |
| TOTAL COMPOSITION | 100% | 213.0 |

*Methocel ® E50, Dow Chemical Company

Methanol was admixed with isopropyl alcohol. The alcohol solution was admixed with water and hydroxypropylmethylcellulose polymer gel and stirred for 2 minutes. The resulting composition did not phase and after hand application, had rub-off characteristics of the preferred embodiment but little cleaning effect.

It will thus be seen that the present invention provides a new and useful cleansing composition, which has a number of advantageous characteristics, including those pointed out herein and others which are inherent in the invention. Preferred embodiments of the invention have been described by way of example, and it is anticipated that modifications may be made to the described form without departing from the spirit of the invention or the scope of the appended claims.

I claim:

1. A spread-on/rub-off, rinse-free cleaner composition comprising:
   (a) a storage stable aqueous hydroxyalkylmethylcellulose polymer gel solution having a spreadable lotion-like consistency;
   (b) a cleaning agent including an alkali metal hydroxide, said alkali metal hydroxide being present in an amount sufficient to provide an overall pH to the composition of between 9.0 to 12.0;
   (c) a volatilizing agent comprising a $C_1$–$C_6$ straight or branched chain alcohol added in an amount sufficient to increase the evaporation rate of said cleaner composition so that it beads-up into soft solid particles and rubs off in less than approximately five minutes; and
   (d) a liquid polyamine, whereby said cleaner composition may be spread onto a surface to be cleaned to absorb and extract dirt, oils and foreign particles on said surface and, after exposure to air and after continued rubbing, the viscosity of said cleaner composition rapidly increases causing the cleaner composition and any absorbed or extracted materials to bead up and roll off of said surface without the need for water rinsing or cloth wiping to provide a cleaned surface.

2. A cleaner composition as defined in claim 1, wherein said hydroxyalkylmethylcellulose polymer gel solution comprises hydroxypropylmethylcellulose.

3. A cleaner composition as defined in claim 2, wherein said hydroxypropylmethylcellulose has a viscosity of from about 2,000 to about 5,000 cP. as measured in a 2% solution at 25° C. and has an average particle size greater than about 50 microns.

4. A cleaner composition as defined in claim 1, wherein said cleaning agent further comprises a non-ionic surfactant.

5. A cleaner composition as defined in claim 4, wherein said non-ionic surfactant is an ethylene oxide ester of a $C_9$–$C_{10}$ alkyl phenol.

6. A cleaner composition as defined in claim 1, wherein said cleaning agent further comprises a polymeric polyol.

7. A cleaner composition as defined in claim 1, wherein said polymeric polyol is mono butyl ether or ethylene glycol.

8. A cleaner composition as defined in claim 1, wherein said cleaning agent further comprises a chelating agent.

9. A cleaner composition as defined in claim 8, wherein said chelating agent is a tetrasodium salt of ethylenediamine tetraacetic acid.

10. A cleaner composition as defined in claim 1, further comprising a plasticizer added in an amount sufficient to provide a film-forming substance capable of being applied onto hands to form a flexible, soil-resistant barrier film removable by water rinsing.

11. A cleaner composition as defined in claim 10, wherein said plasticizer is glycerine added in an amount of up to 5.0% by weight, based upon the weight of the overall cleaner composition.

12. A cleaner composition as defined in claim 10, further comprising germicide or bactericide added in an amount sufficient to provide a flexible, germ-proof, soil-resistant barrier film.

13. A cleaner composition as defined in claim 1, wherein said alcohol is selected from the group consisting of methanol or isopropyl alcohol.

14. A cleaner composition as defined in claim 1, wherein said alkali metal hydroxide is selected from the group consisting of lithium hydroxide, sodium hydroxide or potassium hydroxide.

15. A cleaner composition as defined in claim 1, wherein said cleaner composition further includes an emollient in an amount sufficient to enhance the softness of a smooth micro-film remaining on the surface on the skin after the cleaner composition has been rubbed and rolled off.

16. A cleaner composition as defined in claim 1, wherein said liquid polyamine is present in an amount of about 1.0% by weight, based upon the weight of the overall cleaner composition.

17. A method for cleaning hands which comprises:
   applying a spread-on/rub-off, rinse-free cleaner composition to a pair of hands, said cleaner composition including: (a) a storage stable aqueous hydroxyalkylmethylcellulose polymer gel solution having a spreadable lotion-like consistency; (b) a cleaning agent including an alkali metal hydroxide, said alkali metal hydroxide being present in an amount sufficient to provide an overall pH to the cleaner composition of between 9.0 to 12.0; and (c) a volatilizing agent including a $C_1$–$C_6$ straight or branched chain alcohol added in an amount sufficient to increase the evaporation rate of said cleaner composition so that it beads-up into soft solid particles and rubs off in less than approximately five minutes,
   rubbing the hands together for a time sufficient to cause the applied cleaner to bead-up into soft solid particles which collect dirt, grease, oils and foreign matter from the hands; and
   permitting the soft solid particles and collected dirt to fall off the hands leaving a pair of cleaned hands.

18. A method for cleaning carpet or upholstery surface which comprises:
   applying a spread-on/rub-off, rinse-free cleaner composition to said surface, said cleaner composition including: (a) a storage stable aqueous hydroxyalkylmethylcellulose polymer gel solution having a spreadable lotion-like consistency; (b) a cleaning agent including an alkali metal hydroxide, said alkali metal hydroxide being present in an amount sufficient to provide an overall pH to the cleaner composition of between 9.0 to 12.0; and (c) a volatilizing agent including a $C_1$-$C_6$ straight or branched chain alcohol added in an amount sufficient to increase the evaporation rate of said cleaner composition so that it beads-up into soft solid particles and rubs off in less than approximately five minutes, rubbing said applied cleaner composition for a time sufficient to cause the cleaner composition to bead-up into soft adherent solid particles which collect dirt and foreign matter from said surface, and brushing or vacuuming said solid particles off said surface to provide a cleaned surface.

19. A method for making a temporary polymer barrier coating on hands which comprises:

applying a flexible film-forming barrier composition onto the hands to form a coating, said barrier composition including: (a) a storage stable aqueous hydroxyalkylmethylcellulose polymer gel solution having a spreadable lotion-like consistency; (b) a cleaning agent including an alkali metal hydroxide, said alkali metal hydroxide being present in an amount sufficient to provide an overall pH to the cleaner composition of between 9.0 to 12.0; (c) a volatilizing agent including a $C_1$-$C_6$ straight or branched chain alcohol added in an amount sufficient to increase the evaporation rate of said cleaner composition so that it beads-up into soft solid particles and rubs off in less than approximately five minutes; and (d) a plasticizer added in an amount sufficient to provide a flexible, film-forming barrier composition, and permitting the barrier composition to cure to form an adherent flexible film glove removable by water rinsing.

* * * * *